(12) United States Patent
Washington

(10) Patent No.: US 11,992,667 B2
(45) Date of Patent: May 28, 2024

(54) MANDIBULAR ANESTHESIA CURVED DENTAL NEEDLE

(71) Applicant: Jelani T. Washington, Conyers, GA (US)

(72) Inventor: Jelani T. Washington, Conyers, GA (US)

( * ) Notice: Subject to any disclaimer, the term of this patent is extended or adjusted under 35 U.S.C. 154(b) by 707 days.

(21) Appl. No.: 16/848,731

(22) Filed: Apr. 14, 2020

(65) Prior Publication Data

US 2021/0316083 A1 Oct. 14, 2021

(51) Int. Cl.
| | |
|---|---|
| *A61M 5/32* | (2006.01) |
| *A61M 5/28* | (2006.01) |
| *A61M 5/34* | (2006.01) |
| *A61M 19/00* | (2006.01) |

(52) U.S. Cl.
CPC .......... *A61M 5/3286* (2013.01); *A61M 5/288* (2013.01); *A61M 5/345* (2013.01); *A61M 19/00* (2013.01); *A61M 2202/048* (2013.01); *A61M 2210/0631* (2013.01)

(58) Field of Classification Search
CPC ........ A61M 2210/0631; A61M 5/3286; A61M 5/288; A61M 19/00; A61M 2202/048; A61M 2210/0637
See application file for complete search history.

(56) References Cited

U.S. PATENT DOCUMENTS

| 5,514,113 A | * | 5/1996 | Anderson | ............... A61M 5/32 |
| | | | | 433/90 |
| 6,162,202 A | * | 12/2000 | Sicurelli | .................. A61C 5/40 |
| | | | | 604/525 |
| 2014/0031747 A1 | * | 1/2014 | Ardehali | ............. A61M 5/2425 |
| | | | | 604/112 |
| 2016/0354326 A1 | * | 12/2016 | Uzbelger Feldman | ..................... |
| | | | | A61K 31/381 |

FOREIGN PATENT DOCUMENTS

WO WO-2016185212 A1 * 11/2016 ............. A61M 5/24

OTHER PUBLICATIONS

De St Georges J. How dentists are judged by patients. Dent Today 2004; 23(8): 96-99.

Claffey E, Reader A, Nusstein J, Beck M, Weaver J. Anesthetic efficacy of articaine for inferior alveolar nerve blocks in patients with irreversible pulpitis. JOE. 2004; 30: 568-571.

Levy T.P. An assessment of the Gow-Gates mandibular block for third molar surgery. J AM Dent Assoc 1981; 103: 37-41.

Montagnese T, Reader A, Melfi R. A Comparative study of the Gow-Gates technique and a standard technique for mandibular anesthesia. JOE 1984; 10: 158-163.

(Continued)

*Primary Examiner* — Ariana Zimbouski
*Assistant Examiner* — Rachel T. Smith
(74) *Attorney, Agent, or Firm* — E J Asbury III, LLC

(57) ABSTRACT

The present invention provides a curved needle design which deflects to an advantageous angle when inserted within the medial posterior soft tissue of the patient lower (Continued)

jaw. The deflected needle tip is more perpendicular to the vertical wall of the posterior ramus and promotes the needle tip contacting bone proximate to the inferior alveolar nerve prior to injection of anesthetic. The needle design also improves the tactile feedback to the dental practitioner as the needle penetrates tissue and contacts bone.

12 Claims, 13 Drawing Sheets

(56) References Cited

OTHER PUBLICATIONS

Quinn CL. Injection to anesthetize the difficult tooth. J Calif Dent Assoc. 1998; 26: 665-667.

Manski MC, Cartee DL. Tips for administering inferior alveolar nerve block. Dimensions of Dental Hygiene. 2018: 13(11); 60-63.

Delgado-Molina E, Tamarit-Borras M, Berini-Ayetes L, Gay-Escoda C. Comparative study of two needle models in terms of deflection during inferior alveolar nerve block. Med Oral Patol Oral Cir Bucal. Sep. 1, 2009; 14 (9): e440-4.

Kenedy S, Reader A, Nusstein J, Beck M, Weaver J. The significance of needle deflection in success of the inferior alveolar nerve block in patients with irreversible pulpitis. JOE. 2003; 29: 630-633. 2003.

Haas DA, Alternative mandibular nerve lock techniques: A review of the Gow-Gates and Akinosi-Vazirani closed-mouth mandibular nerve block techniques. JADA. 2011; 142(9 suppl): 8S-12S.

Reed K, Malamed S, Fonner. Local Anesthesia Part 2: Technical Considerations. Anesth Prog. 2012; 59: 127-137.

Shahi S, Rahimi S, Yavari HR, Ghasemi N, Ahmadi F. Success rate of 3 injection methods with articaine for mandibular first molars with symptomatic irreversible pulpitis: A consort randomized double-blind clinical trial. JOE. 2018; 44: 1462-1466.

Palti DG, de Almeida CM, Rodrigues A, Andreo JC, Oliveira JE. Anesthetic technique for inferior alveolar nerve block: a new approach. J Appl Oral Sci. 2011; 19(1): 11-15.

* cited by examiner

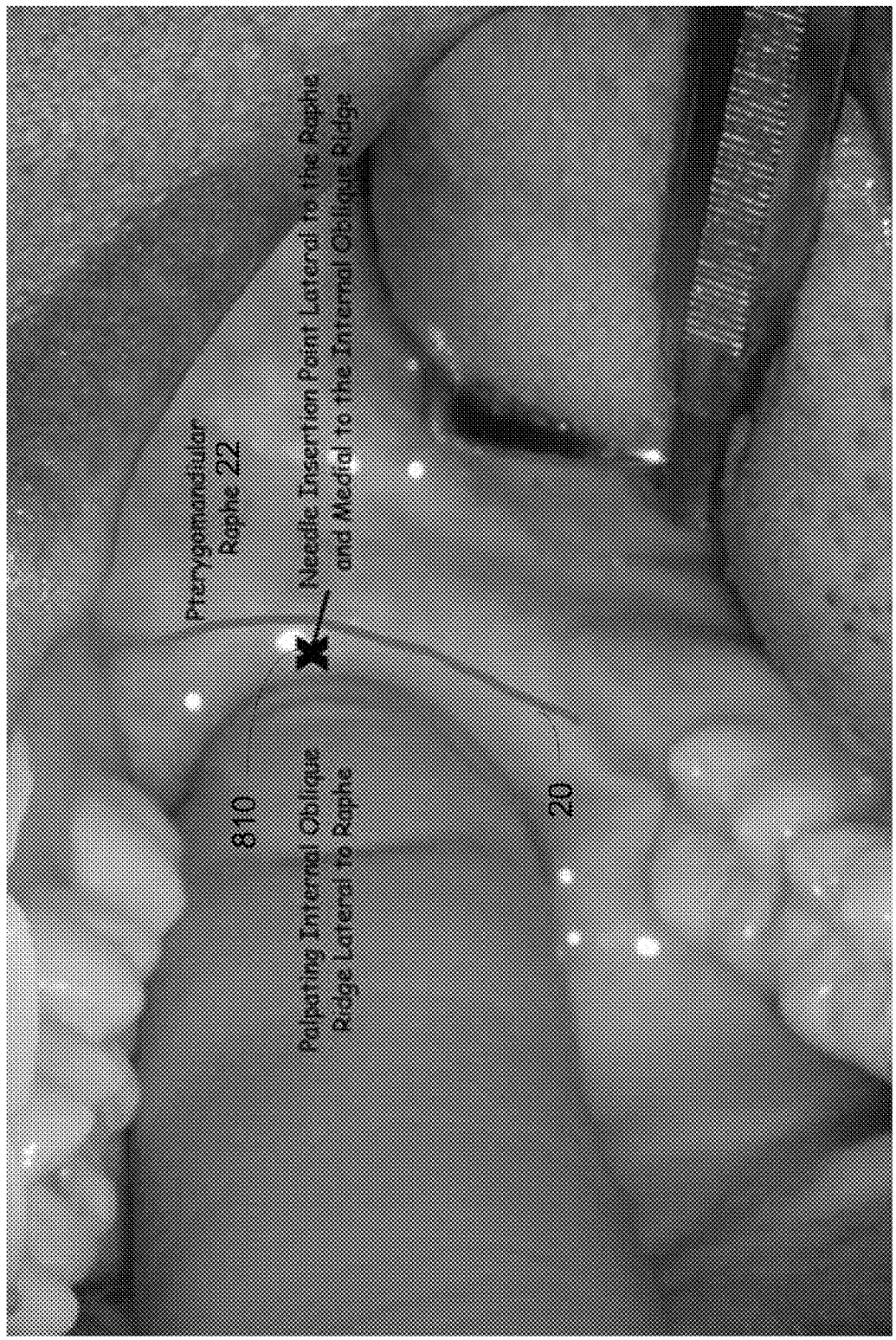

MANDIBULAR ANESTHESIA CURVED DENTAL NEEDLE

REFERENCES CITED

Other Publications

1 De St Georges J. How dentists are judged by patients. Dent Today 2004; 23(8):96-99.
2. Claffey E, Reader A, Nusstein J, Beck M, Weaver J. Anesthetic efficacy of articaine for inferior alveolar nerve blocks in patients with irreversible pulpitis. JOE. 2004; 30:568-571.
3. Levy T. P. An assessment of the Gow-Gates mandibular block for third molar surgery. J AM Dent Assoc 1981; 103:37-41.
4. Robertson W E. Clinical evaluation of mandibular conduction anesthesia. Gen Dent 1979; 27:49-51.
5. Montagnese T, Reader A, Melfi R. A Comparative study of the Gow-Gates technique and a standard technique for mandibular anesthesia. JOE 1984; 10: 158-163.
6. Quinn C L. Injection to anesthetize the difficult tooth. J Calif Dent Assoc. 1998; 26:665-667.
7 Bassett K B, DiMarco A C, Naughton D K. Local Anesthesia for Dental Professionals. 2nd ed. Upper. Saddle River, NJ. Pearson Prentice Hall: 2014.
8. Malamed S F. Handbook of Local Anesthesia. 6th ed. St. Louis, Mo. Elsevier Mosby: 2013.
9. Evers H, Haegerstam G. Introduction to Dental Local Anesthesia. 2nd ed. Fribourg, Switzerland: Mediaglobe SA; 2003.
10. Manski M C, Cartee D L. Tips for administering inferior alveolar nerve block. Dimensions of Dental Hygiene. 2018:13(11); 60-63.
11. Bassett, K. B. (2010). Local Anesthesia for Dental Professionals (pp. 330). Pearson Education, Inc.
12. Malamed, S. G. (2004). Handbook of local anesthesia (5th ed., pp. 227-253). St. Louis: Elsevier Mosby.
13. Delgado-Molina E, Tamarit-Borras M, Berini-Ayetes L, Gay-Escoda C. Comparative study of two needle models in terms of deflection during inferior alveolar nerve block. Med Oral Patol Oral Cir Bucal. 2009 Sep. 1; 14 (9):e440-4.
14. Kenedy S, Reader A, Nusstein J, Beck M, Weaver J. The significance of needle deflection in success of the inferior alveolar nerve block in patients with irreversible pulpitis. JOE. 203; 29:630-633.
15. Haas D A, Alternative mandibular nerve lock techniques: A review of the Gow-Gates and Akinosi-Vazirani closed-mouth mandibular nerve block techniques. JADA. 2011; 142(9 suppl):8S-12S.
16. Reed K, Malamed S, Fonner. Local Anesthesia Part 2: Technical Considerations. Anesth Prog. 2012; 59:127-137.
17. Shahi S, Rahimi S, Yavari H R, Ghasemi N, Ahmadi F. Success rate of 3 injection methods with articaine for mandibular first molars with symptomatic irreversible pulpitis: A consort randomized double-blind clinical trial. JOE. 2018; 44:1462-1466.
18. Palti D G, de Almeida C M, Rodrigues A, Andreo J C, Oliveira J E. Anesthetic technique for inferior alveolar nerve block: a new approach. J Appl Oral Sci. 2011; 19(1):11-15.

BACKGROUND OF THE INVENTION

1. Field of the Invention

The present invention relates generally to needles used in the injection of pharmaceutical drugs during dental procedures. More specifically, the present invention has effective application in the lower jaw injection of mandibular anesthesia during dental procedures.

2. Description of the Related Art

Sound local anesthesia technique is a corner-stone of dentistry. Some of the most common statements heard are: "Do I have to get a shot?" or "Just don't show me the needle!" or "I'm fine after the needle." De St Georges, an internationally renowned dental practice management speaker and author, surveyed her audiences on how they perceived dentists[1]. She identified 20 key areas. On that list, the second most important area of concern was that the procedure "does not hurt"[1]. The most important area of concern was "a painless injection"[1]. When you consider comments by patients, the two most common areas of concern involve pain. Therefore, the importance of sound anesthesia administration technique and accuracy cannot be underestimated.

As depicted in FIG. 1, a particular problematic injection site is to the mandible (lower jaw 10). Mandibular anesthesia success rates have been shown to range from as low as 19% to as high as 98%[2-6] depending on the criteria for success. This wide range of dental anesthesia success suggests there is a degree of ambiguity with the technique and/or a deficiency in instrument design used to attempt mandibular anesthesia. The most common technique taught is the Halstead technique. As the mandibular nerve descends from the Trigeminal ganglion it makes several branches, one of which is the inferior alveolar nerve 12 (primary nerve of the lower jaw). It is the inferior alveolar nerve that is anesthetized before it enters the Mandibular foramen 14. In the Halstead technique, a syringe needle tip is used to gain proximity to the mandibular foramen 14 where the inferior alveolar nerve enters the mandible. Also depicted in FIG. 1, are the caronoid notch 16, lingula 18 and internal oblique ridge 20 (boney wall anterior to the opening into the lower jaw for the primary nerve of the lower jaw).

As depicted in FIGS. 2A and 2B, the injection site 24 of the Halstead technique is performed by the dental practitioner by locating several physical landmarks including the coronoid notch 16 (depression along the anterior surface of the ramus), and the lateral depression of the pterygomandibular raphe 22. Also depicted in FIG. 2B are the facial nerve 26, lingual nerve 28, medial surface of the ramus mandible 30, and the masseter muscle 32.

As further depicted in FIGS. 3, 4A, 4B, and 4C once the landmarks are identified, the syringe barrel 40 is oriented over the opposite side premolars 34 (teeth between molar and canine teeth) at an angle parallel to and above the mandibular molar occlusal plane 36 (imaginary plane formed by the chewing surfaces of adjacent teeth), and the beveled tip 44 of a 25 or 27 gauge, straight 35 mm needle 42 is inserted in the mucous membrane lateral (next to, away from the midline, the pterygomandibular raphe) to the pterygomandibular raphe until it contacts bone directly over the nerve as it enters the mandibular foramen (opening of the lower jaw bone for the primary nerve of the lower jaw), at injection site 24[7-10]. As depicted in FIGS. 4B-4C, failure to contact bone is often related to mandibular ramus flare (the external rotation of the posterior vertical wall of the lower jaw) and then requires re-orientation of the needle.

The objective of the needle insertion is to deposit anesthetic in close proximity to the inferior alveolar nerve to provide nerve anesthesia to the teeth and soft tissue along the nerve's path of innervation. A common problem, however, is the aforementioned wide range of anesthetic success. The Halstead technique makes several assumptions: there are contralateral premolar teeth (opposite side teeth), there is a definitive ipsilateral occlusal table (same side chewing surface), the ramus does not flare, the opening in the mandible for the nerve is in a consistent location and that the practitioner can identify the boney and soft tissue physical landmarks.

As depicted in FIGS. 4A, 4B, and 4C, when using a straight, beveled-needle, depending on the flare of the ramus, the needle may or may not contact bone. If the needle contacts bone prematurely as depicted in FIG. 4A, or does not contact bone at all as depicted in FIG. 4B, 4C, the anesthetic may not be deposited close enough to the mandibular foramen. At that point, the needle is retracted, the angle of needle insertion is adjusted, and the needle re-inserted. Often, the needle is deflected away from the intended area of deposition. As a result of this deflection, the chance of successful anesthesia injection is reduced. The wide range of success can be attributed to multiple factors including: anatomical variations[11], volume of anesthetic[11], technique proficiency, and needle deflection[12,13,14] just to name a few.

The deficiency in predictability has brought about a need for alternative techniques to achieve mandibular anesthesia. For example: the Gow-Gates technique[5,15,16] the Vazirani-Akinosi technique[15,16] and modifications to the traditional Halstead technique[17,18]. However, these various techniques also present the same challenges that may encourage a range of success. Until now, attempts to improve the predictability of mandibular anesthesia have been centered around the technique. The instrument used to deliver the anesthetic, the needle, should be addressed.

Needle deflection plays a key role when considering problems with inadequate dental anesthesia injection and should be considered an important aspect in how a dental needle is used during the delivery of anesthetic. As depicted in FIG. 4, once a needle is inserted into soft tissues of the oral cavity, and particularly when considering an inferior alveolar (primary nerve of the lower jaw) nerve block, depending on the physical landmarks encountered or lack-there-of, the needle is often adjusted to compensate and will deflect towards or away from the intended site of injection. This deflection makes a significant contribution to the variability in anesthetic success. In practice, the more significant the needle angle adjustment, the more significant the deflection and variability in the actual anesthetic injection location.

Accordingly, what is needed in the art is a needle designed to actively influence needle deflection towards the intended site of anesthetic deposition. The needle design should promote injection of the anesthetic proximate to the nerve without reposition or adjustment of the needle injection angle required. It is thus to such a needle design that the present invention is primarily directed.

SUMMARY OF THE INVENTION

The disadvantages of the prior art are overcome by the present invention which, in one aspect, is a needle assembly used in dental procedures upon a patient. The needle assembly is affixed to a syringe barrel for use. The syringe barrel houses a carpule containing a pharmaceutical compound. The needle assembly having a shaft with a central bore therein for passing pharmaceutical chemicals there thru. The shaft has a tip on one end which is in fluid interconnection with the central bore. The needle assembly also has a hub and a syringe adaptor. The needle shaft passes thru the hub and syringe adaptor and configured to engage the syringe barrel. The needle shaft extends beyond the syringe adaptor and is configured to pierce the carpule upon engagement with the syringe barrel. The central bore of the needle shaft and the tip are thereby in fluid interconnection with the pharmaceutical compound contained in the carpule.

The needle shaft includes a curve therein such that the centerline axis of the shaft at the tip is at an angle when compared to the centerline axis of the shaft at the hub.

Wherein, as the needle tip is inserted into an injection site in the patient and an axial force is applied to the syringe barrel, the centerline axis of the shaft at the needle shaft tip deflects to a more advantageous angle for injection of the pharmaceutical compound proximate to the intended injection site.

In another aspect, the pharmaceutical compound is an anesthetic and the dental procedure is an inferior alveolar nerve block. The angled tip of the needle assembly facilitates access to the injection site by avoiding physical obstacles presented by the patient anatomy to the needle assembly and syringe.

In another aspect, the angle between the centerline axis of the shaft at the tip when compared to the centerline axis of the shaft at the hub is between 15 and 45 degrees, and preferably 30 degrees. The needle shaft has an internal gauge between 20 and 32. Preferably, the needle shaft has an internal gauge between 25 to 27. The shaft has a length between 20 millimeters to 40 millimeters from tip to hub measured along the shaft centerline and preferably a length of thirty-five millimeters from tip to hub measured along the shaft centerline.

The needle tip includes a single axial hole and angled tip. The needle tip further includes at least one port in fluid interconnection with the needle fluid passage for delivery of the chemical compound. In another aspect, the needle tip may not have an axial hole, but has a plurality of ports in fluid interconnection with the needle fluid passage for delivery of the chemical compound.

In yet another aspect, the present invention provides a dental procedure for injection of anesthetic into a patient's jaw in an inferior alveolar nerve block. The procedure utilizing a needle assembly affixed to a syringe. The needle assembly includes a needle shaft with a central bore therein for passing pharmaceutical chemicals there thru. The needle assembly includes a tip on one end in fluid interconnection with the central bore. The needle assembly also includes a hub and a syringe adaptor, the needle shaft passing thru the hub and syringe adaptor. The syringe adaptor configured to engage the syringe barrel. The needle shaft extending beyond the syringe adaptor and configured to pierce the carpule upon engagement with the syringe barrel. The central bore of the needle shaft and the tip thereby in fluid interconnection with the pharmaceutical compound contained in the carpule.

The needle assembly including the needle shaft having a bend therein such that the centerline axis of the shaft at the tip is at an angle when compared to the centerline axis of the shaft at the hub. Wherein, during the injection procedure as the needle tip is inserted into an injection site in the patient an axial force is applied to the syringe barrel. The centerline axis of the needle shaft at the tip deflects to a more advantageous angle for injection of the pharmaceutical compound proximate to the intended injection site. The angled tip of the needle assembly facilitates access to the injection site by avoiding physical obstacles presented by the patient anatomy to the needle assembly and syringe.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE DRAWINGS

FIG. 8A is a side perspective view of the human mouth with landmarks used in the injection of anesthesia with the present invention.

DETAILED DESCRIPTION OF THE INVENTION

The present invention provides a curved needle design which deflects to an advantageous angle when inserted within the medial posterior soft tissue of the patient's lower jaw. The deflected needle tip is more perpendicular to the vertical wall of the posterior ramus and promotes the needle tip contacting bone proximate to the inferior alveolar nerve prior to injection of anesthetic. The needle design also improves the tactile feedback to the dental practitioner as the needle penetrates tissue and contacts bone.

Figure 5:
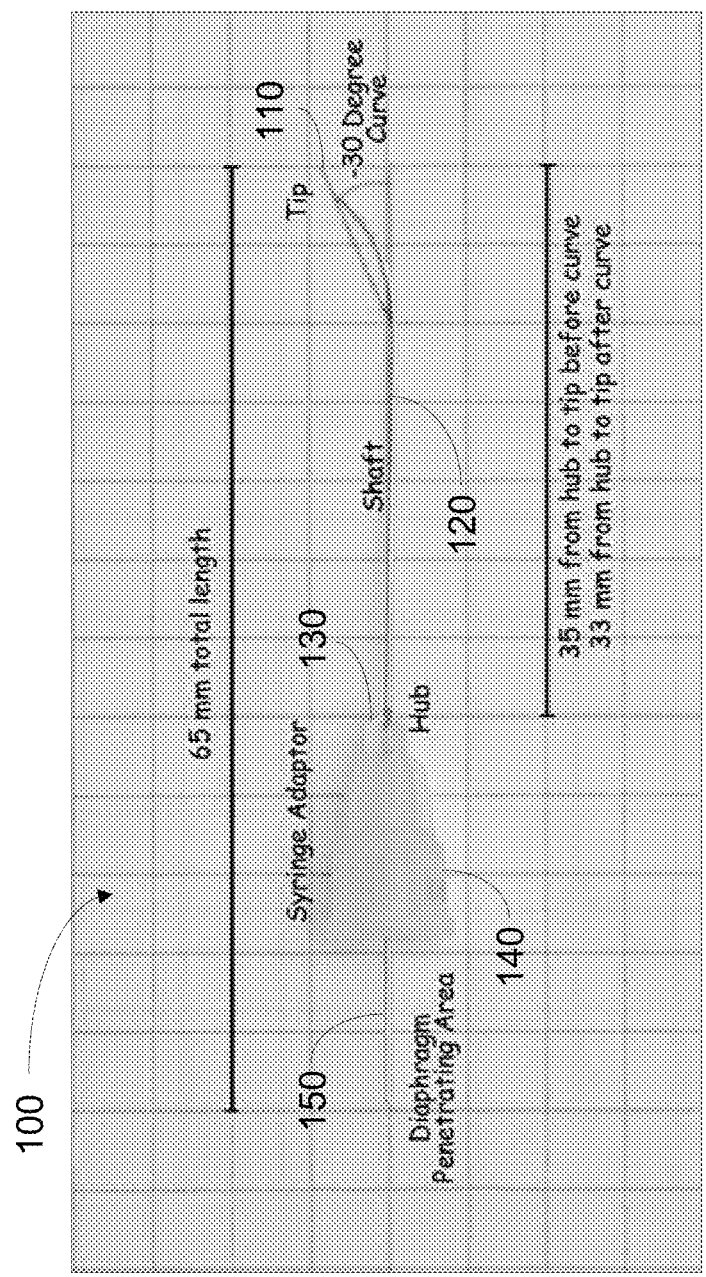
FIG. 5 is a side view of the components of the angled needle of the present invention.

As depicted in FIG. 5, the dental anesthetic needle assembly of the present invention is composed of a continuous length of stainless steel. There are five key features/components of the needle assembly 100 of the present invention. The needle assembly includes the tip 110, the shaft 120, the hub 130, syringe adaptor 140 and, the diaphragm penetrating area 150.

As further depicted in FIG. 5, the portion of the shaft 120 proximate to the tip 110 that will penetrate soft tissue is curved to a preferable 30 degree angle. The curve of the shaft 120 may be continuous along the shaft between the hub 130 and tip 110 to end in a tip angled in relation to the centerline of the shaft at the hub, or the curve may be formed by a more abrupt small radius bend along the length of the shaft 120, or any combination thereof. The curve in the needle shaft 120 is accomplished without collapsing or substantially reducing the internal bore of the needle thru which anesthesia or other pharmaceutical compounds are passed. In a first embodiment depicted in FIGS. 5-6, the shaft 120 has a substantially straight portion adjacent the hub 130, and a substantially straight portion adjacent the tip 110, with a curve there-between to form an angle between the centerline axis of the shaft at the tip, and the centerline axis of the shaft at the hub. In other alternative embodiments, the angle formed between the centerline axis of the shaft 120 at the tip 110, and the centerline axis of the shaft 120 at the hub 130 may be between 15 and 45 degrees.

In the first embodiment, the shaft measures a length of thirty-five millimeters from tip 110 to hub 130 measured along the shaft 120 centerline. The shaft 120 has a twenty-five or twenty-seven gauge internal diameter and 0.4 to 0.5 millimeter outer diameter. As will be appreciated by those skilled in the art, thirty and thirty two millimeter shafts are also considered long needles, whereas twenty and twenty-five millimeter shafts are also considered short needles. In alternative embodiments, the shaft may be between 20 millimeters to 40 millimeters in length, and the shaft may have a 20 to 32 internal gauge. In other alternative embodiments, the internal needle gauge and/or the needle outer diameter may vary along the needle length.

Figure 6A:
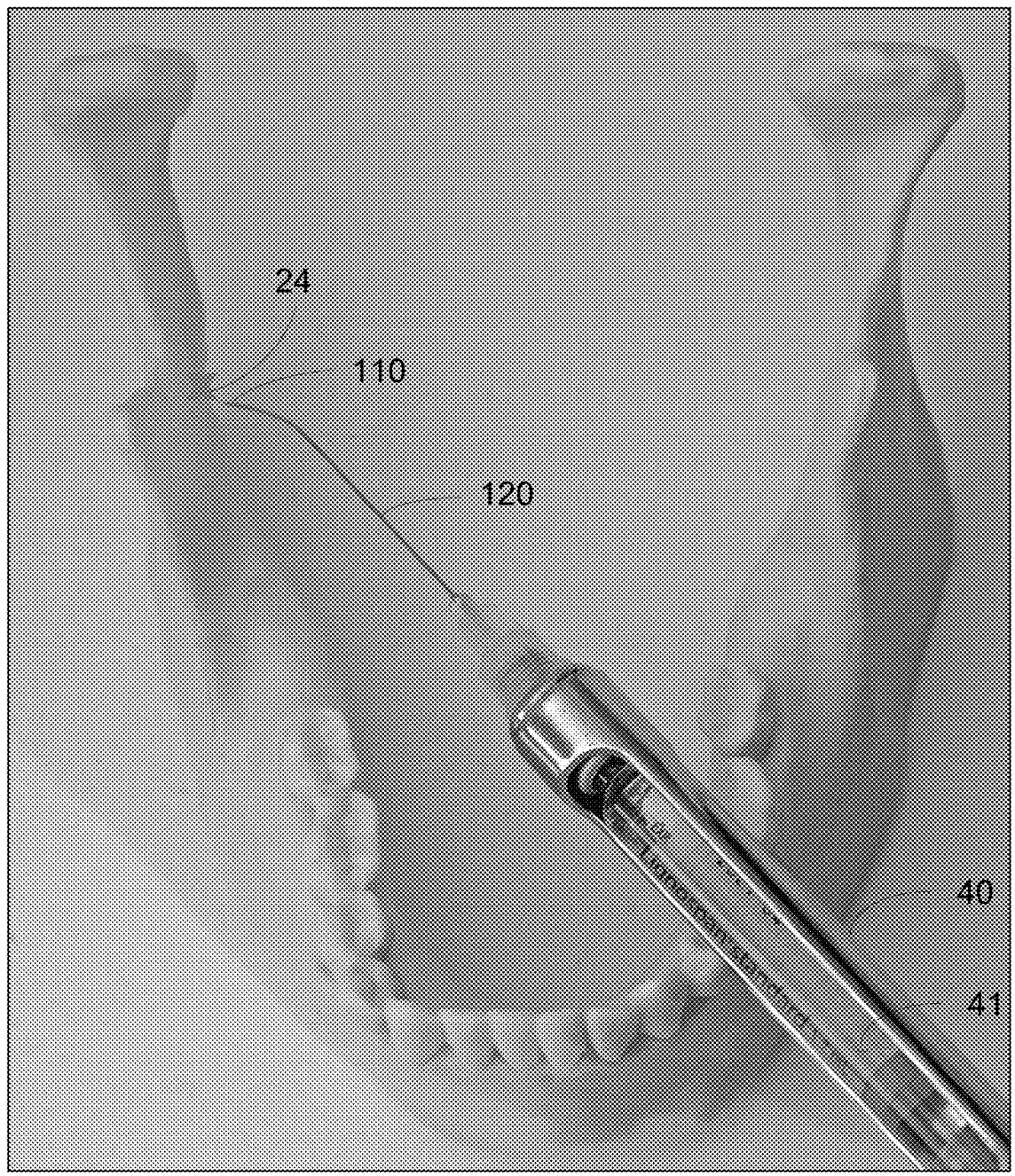
FIGS. 6A, 6B, 6C are perspective views of the lower jaw depicting anesthesia injection by the needle of the present invention.

As depicted in FIGS. 5, 6A, the hub 130 is the component that connects the shaft 120 to the syringe adaptor 140 via adhesive or a press fit in the plastic hub. The plastic syringe adaptor 140 has an internal thread pattern to affix the needle to the syringe barrel. Through the syringe adaptor continues the remaining twenty-five millimeters of the stainless steel needle shaft 150 that penetrates the diaphragm of the anesthetic carpule 41. As appreciated by those skilled in the art, in other applications of the present invention the carpule 41 may be filled with other pharmaceutical compounds. As further appreciated by those skilled in the art, the curved needle design of the present invention may be used with other syringe designs, for example single use disposable syringes. The needle assembly may also engage the syringe via a press fit.

Figure 1:
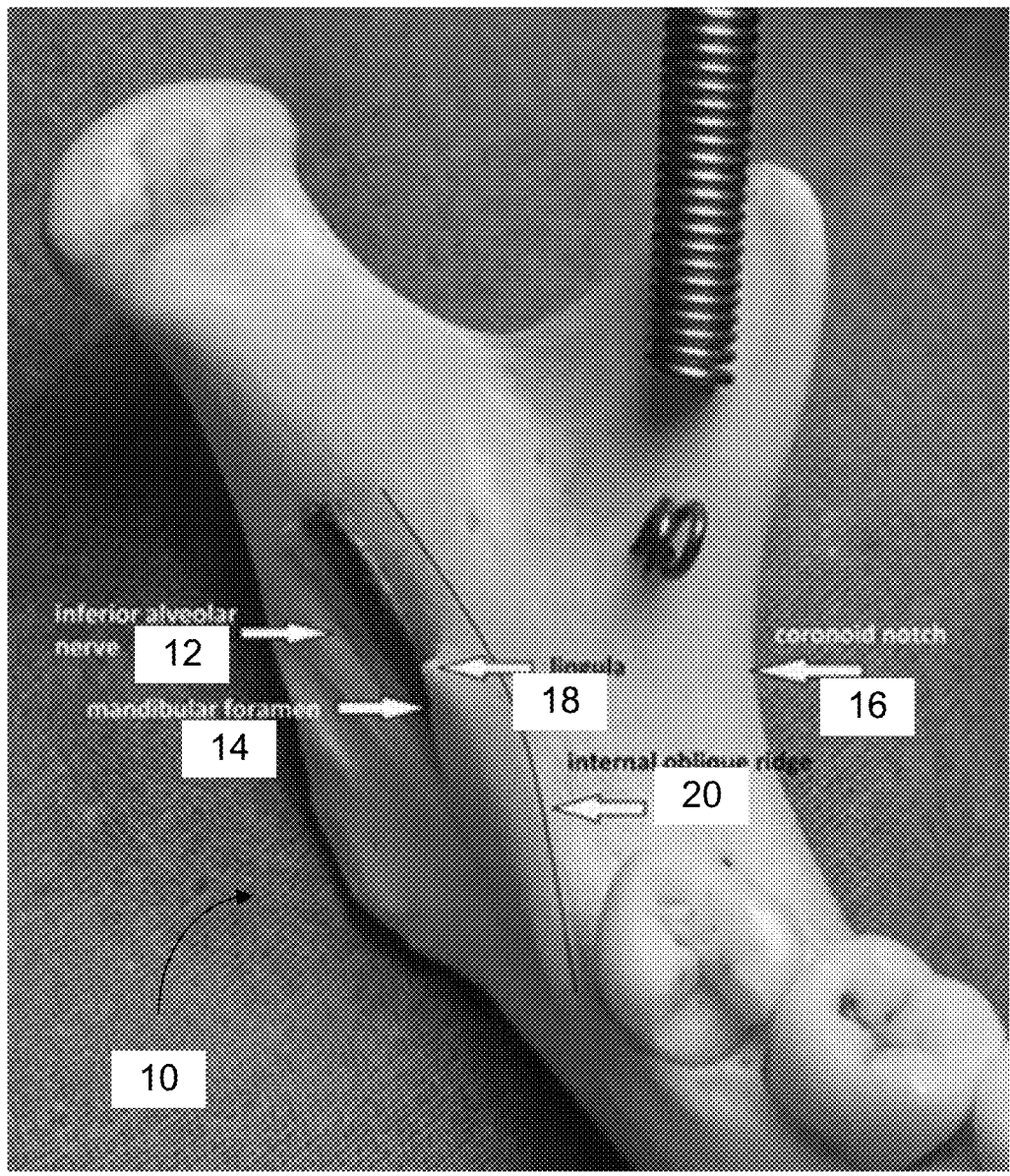
FIG. 1 is a side-perspective view of the human lower jaw.
Figure 2A:
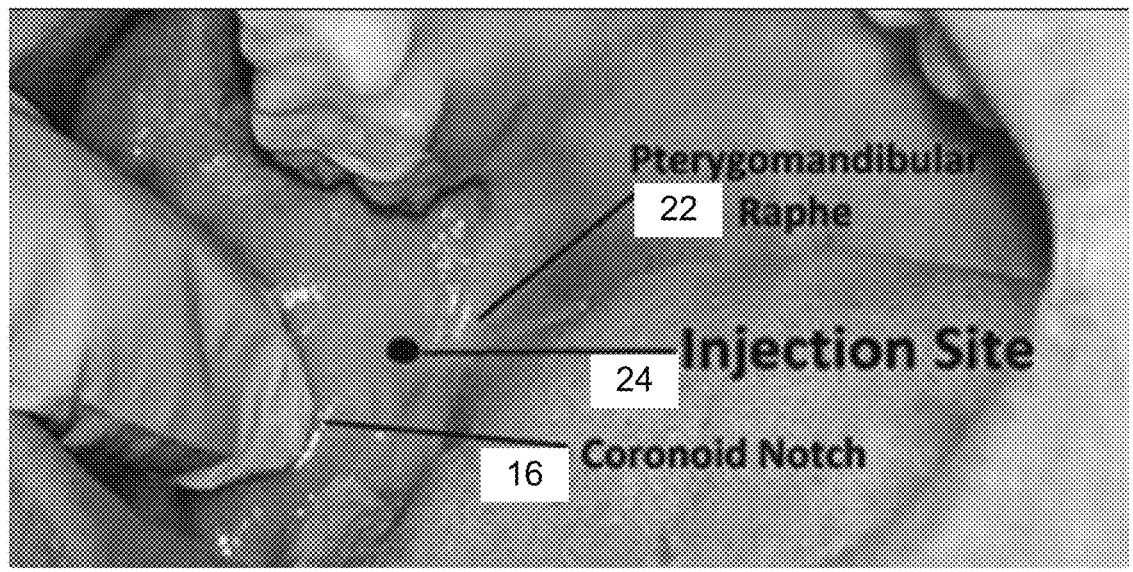
FIG. 2A is a side view of the human mouth with landmarks used in the injection of anesthesia.
Figure 2B:
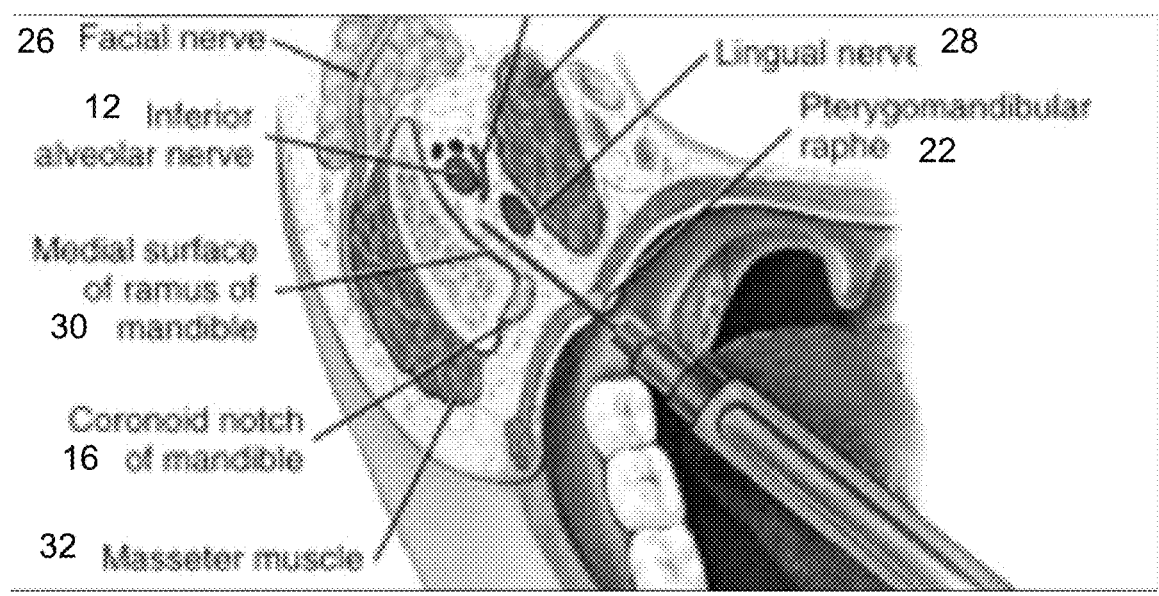
FIG. 2B is a cutaway depiction of the lower jaw with anesthesia injection needle.
Figure 3:
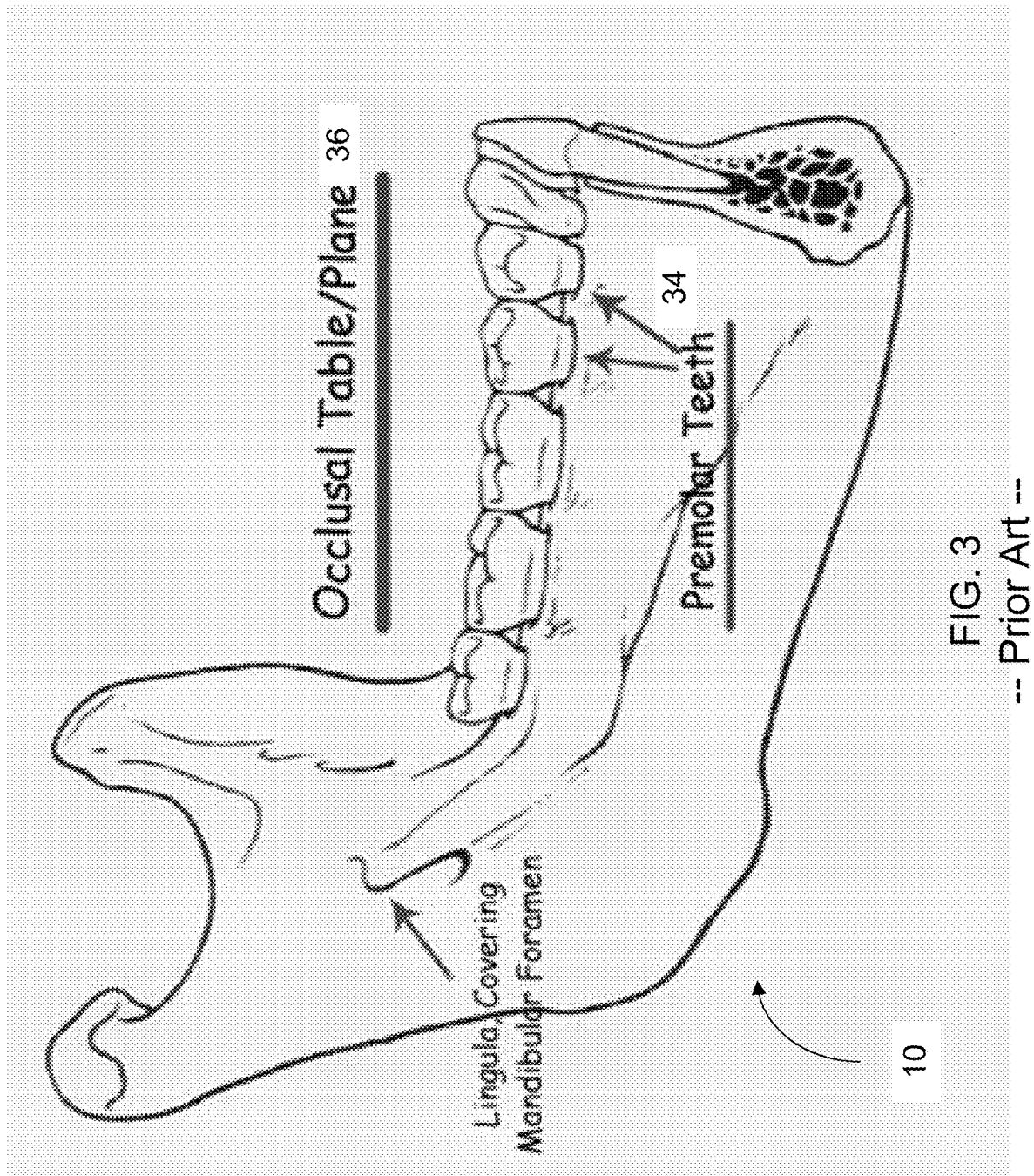
FIG. 3 is a side perspective view of one side of the lower jaw.
Figure 4B:
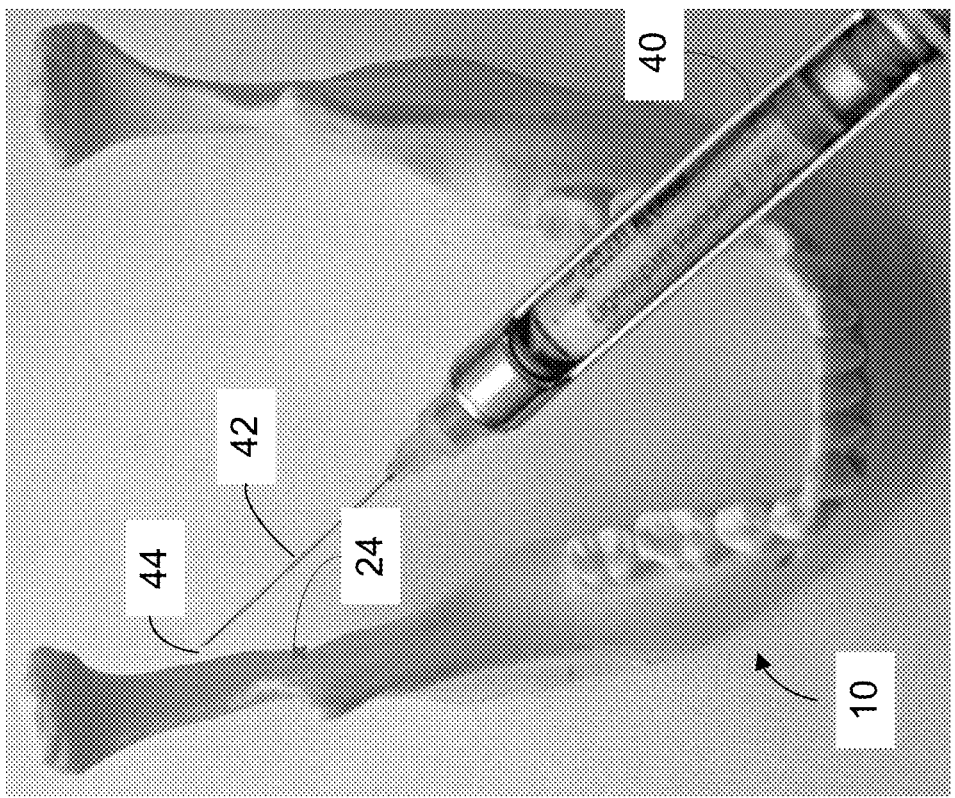
FIGS. 4A, 4B, 4C are perspective views of the lower jaw depicting anesthesia injection by a prior art needle.
Figure 4A:
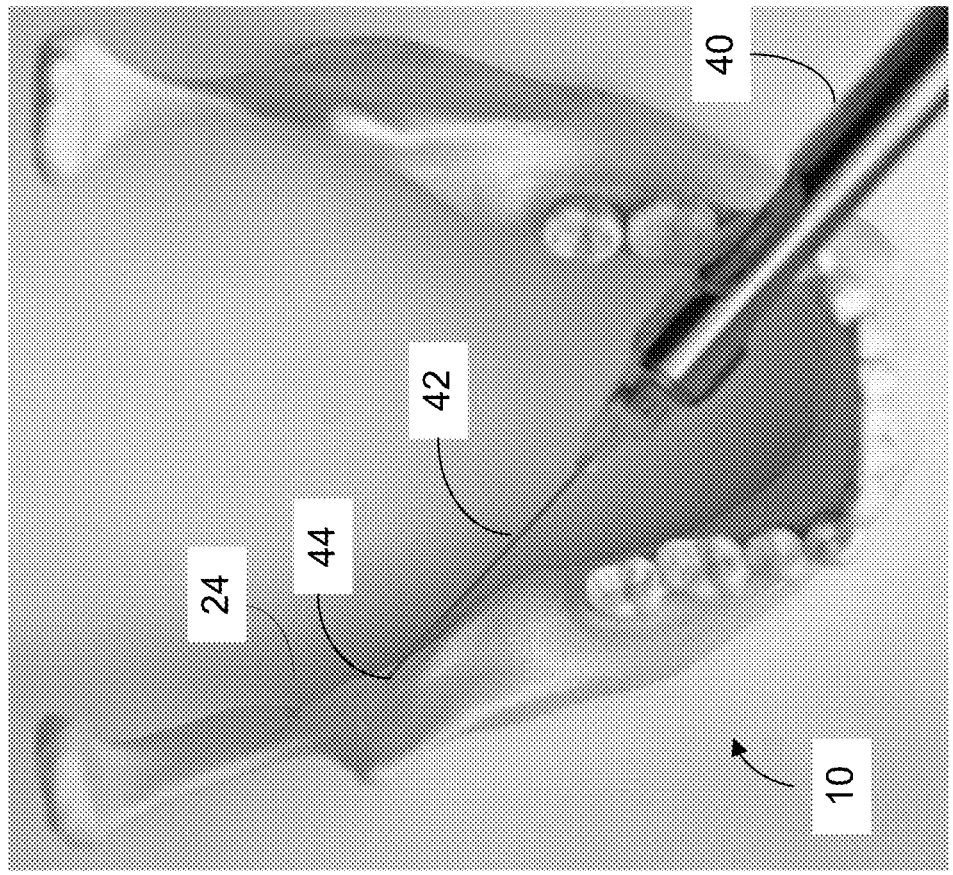
Figure 4C:
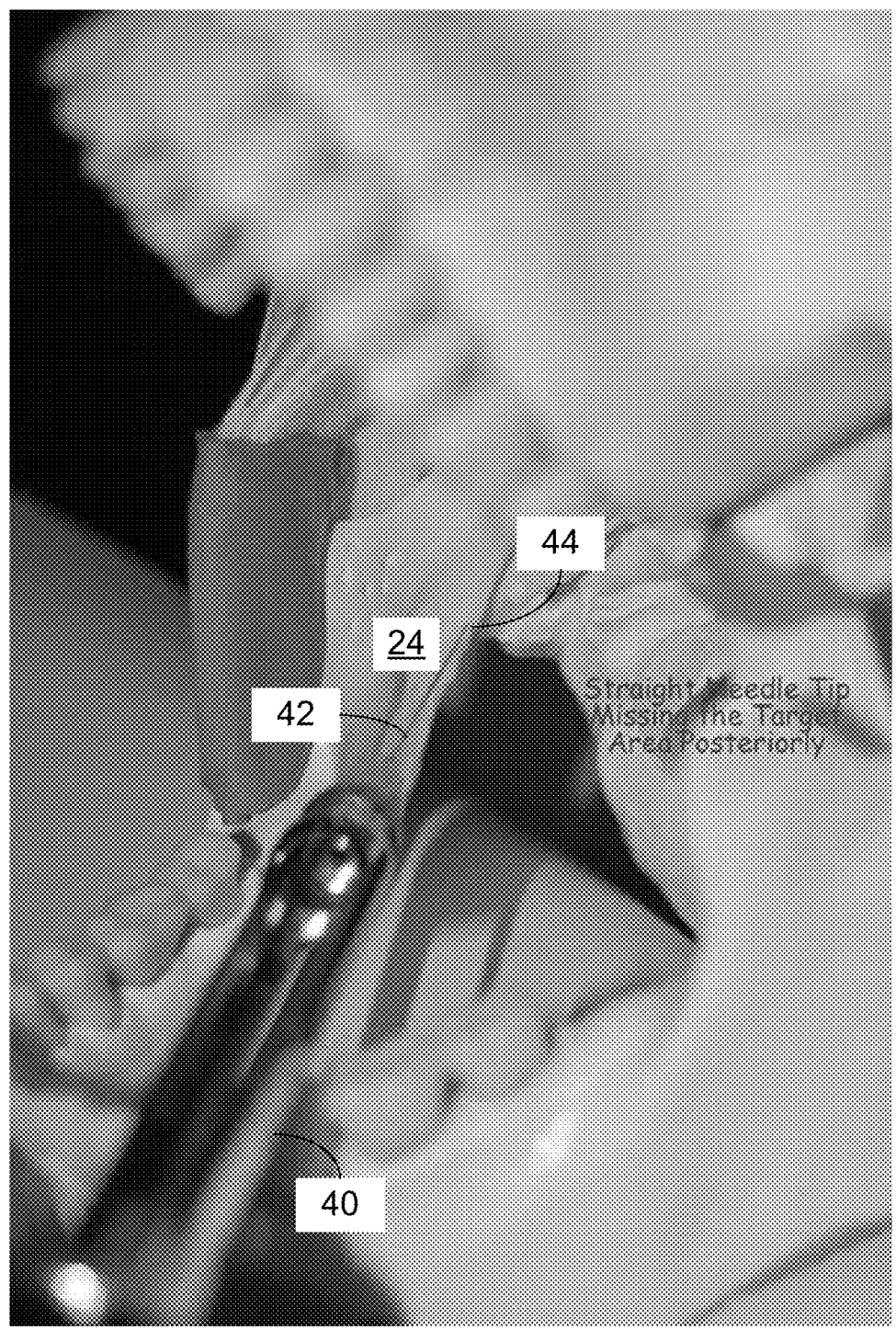
Figure 6B:
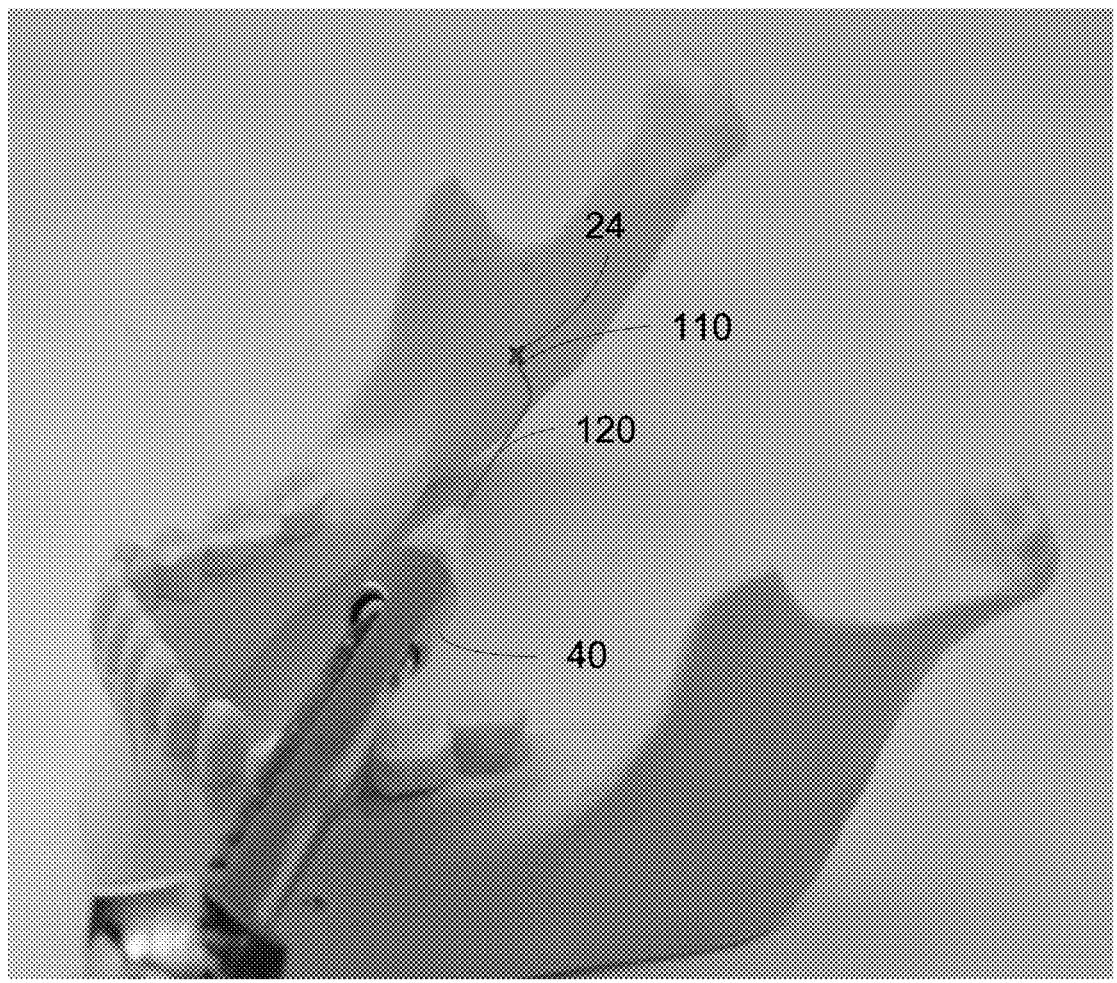
Figure 6C:
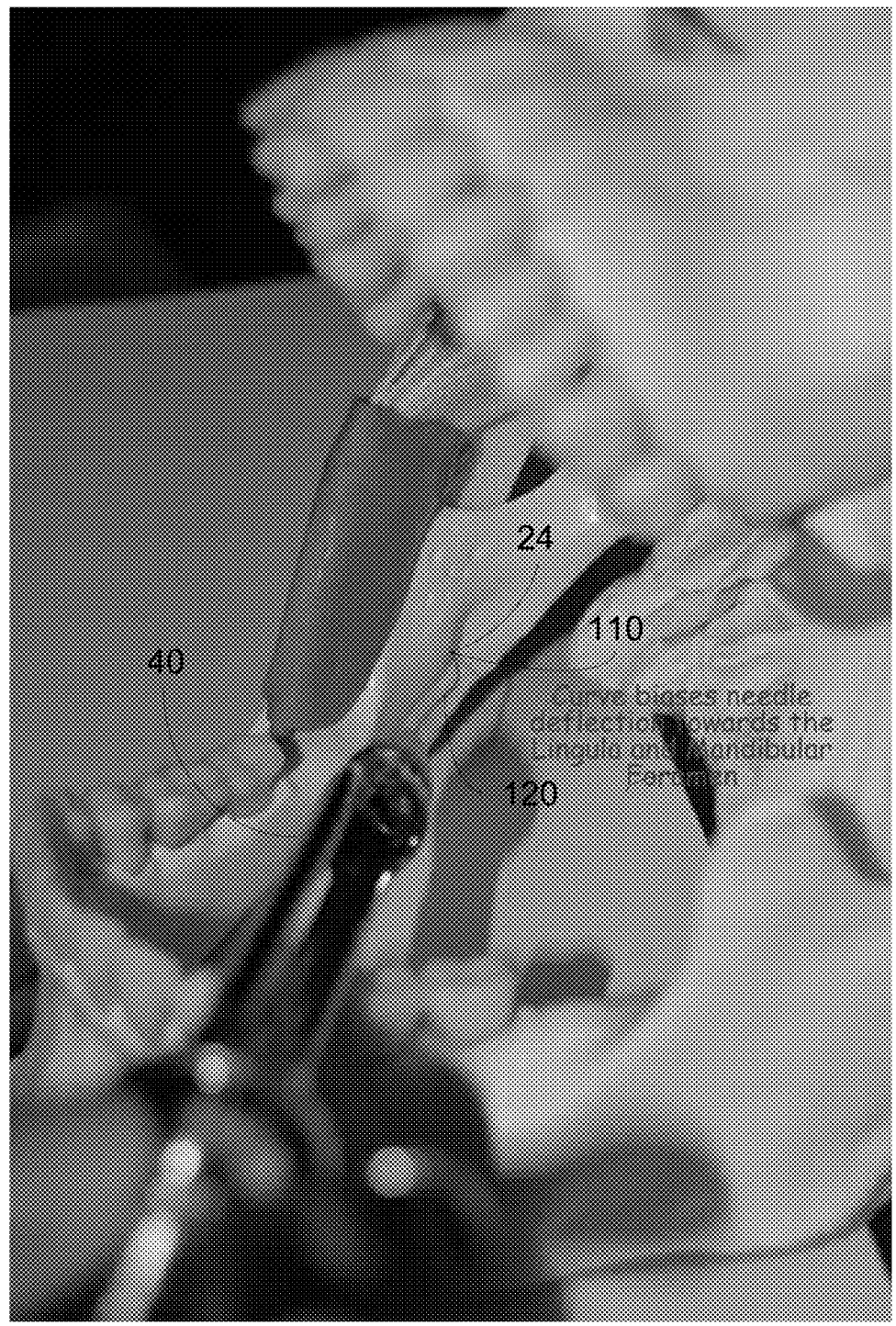

The dental procedure technique of using the needle assembly of the present invention differs over the prior art Halstead technique. As depicted in FIGS. 6A, 6B and 6C, the 30 degree curvature at the tissue penetrating end, tip 110, of the curved needle 100 is incorporated to exploit the concept of needle deflection. The curved or angled needle shaft 120 reduces the variability of anatomical differences between patients, particularly as it relates to mandibular ramus flare, i.e. the external rotation of the posterior vertical wall of the lower jaw. Once the physical landmarks in the patients mouth are identified, the syringe barrel 40 is oriented over the opposite side premolars 34 (teeth between molar and canine teeth) at an angle parallel to and above the mandibular molar occlusal plane (imaginary plane formed by the chewing surfaces of adjacent teeth), and the beveled tip 110 of the curved needle 100 of the present invention is inserted in the mucous membrane lateral (next to, away from the midline, the pterygomandibular raphe) to the pterygomandibular raphe until it contacts bone proximate to the nerve as it enters the mandibular foramen (opening of the lower jaw bone for the primary nerve of the lower jaw), at injection site $24^{7-10}$. As depicted in FIG. 6C, the curved needle shaft 120 biases the needle tip 110 deflection towards the lingula and mandibular foramen. The curved needle 120 design of the present invention also improves the tactile feedback to the practitioner as the needle penetrates tissue and contacts bone. Referring back to prior art FIGS. 4A, 4B and 4C, a straight needle 42 is more likely to miss the anesthesia target area either anteriorly or posteriorly.

Figure 7:
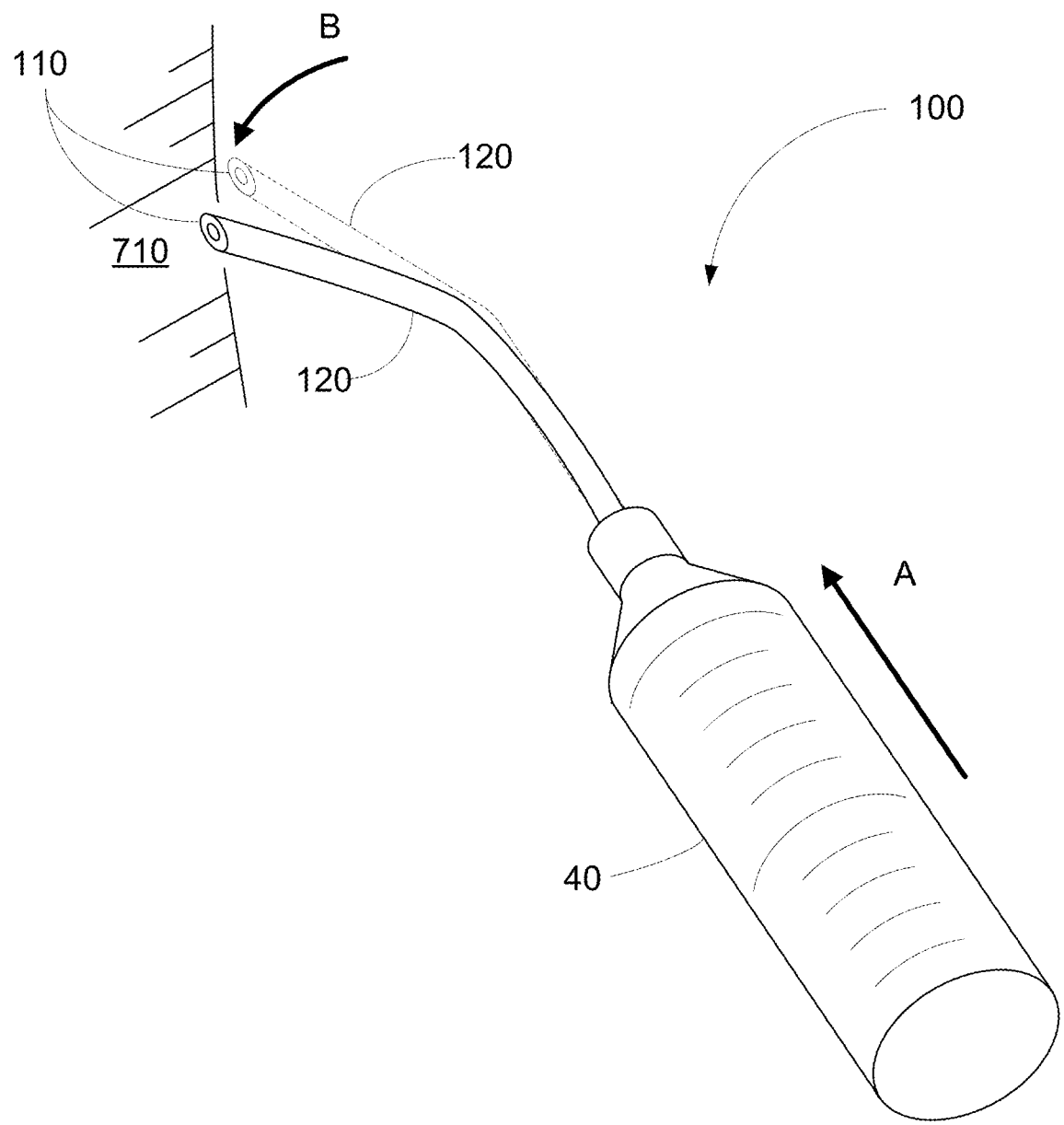
FIG. 7 is a top perspective depiction of anesthesia injection using the angled needle of the present invention.

As depicted in FIG. 7, the curved needle design 100 of the present invention deflects the tip 110 of the needle shaft 120 to be more perpendicular to the posterior vertical wall 710. As pressure is applied axially to the syringe body in the direction of Arrow "A", the centerline axis at the tip 110 of the curved needle shaft 120 is deflected to be more perpendicular to the posterior vertical wall 710 as depicted by curved Arrow "B". Stated another way, the insertion force axially down the center of the syringe body supplied by the dental practitioner is opposed by the offset needle tip 110 and results in a bending moment applied to the needle shaft 120. The bending moment deflects the centerline axis of the needle shaft 120 at the needle tip 110 to be more perpendicular to the posterior vertical wall 710.

Figure 8B:
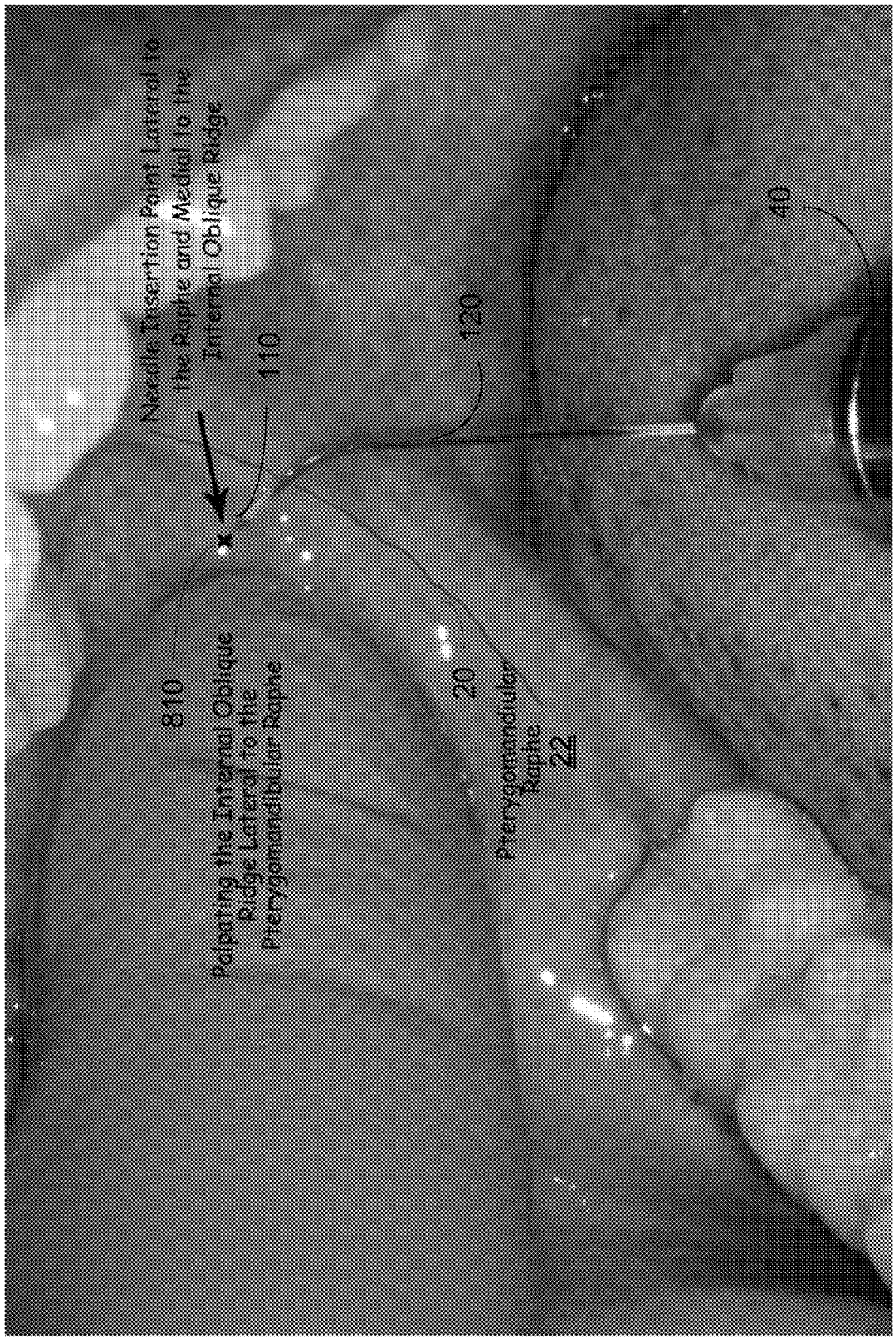
FIG. 8B is a side perspective view of the human mouth with anesthesia injection by the needle of the present invention.

The preferred technique for using the curved needle design 100 is depicted in FIGS. 8A and 8B. The patient is asked to open wide and the pterygomandibular raphe 22 and internal oblique ridge 20 are identified. The internal oblique ridge 20 is depicted by a dashed line in FIGS. 8A and 8B. The wider the patient opens the tighter the tissues covering the internal oblique ridge 20 are stretched. The tight tissues over boney landmarks allow for better manual palpation of landmarks. Once the border of the internal oblique ridge 20 is identified, the clinician palpates the most medial aspect (surface closest to the midline or middle of body) where it begins to transition to the posterior surface (surface facing the back). This step alone eliminates the premature contact of the prior art needle tip 44 with bone as depicted in prior art FIG. 4A. The technique also provides a smaller, more definitive area of where needle insertion site 810 should be to hit the preferred anesthesia injection site 24.

As further depicted in FIG. 8B, in the technique of the present invention the needle tip 110 is inserted at the location 810 medial (towards the midline or middle of body) to the palpated area but lateral (away from the midline or middle of the body) to the pterygomandibular raphe 22 and is simply advanced to contact bone at the medial surface of the ramus. Stated another way, the needle insertion point is lateral to the raphe 22 and medial to the internal oblique ridge 20. No adjustment of the syringe barrel 40 is necessary. The curvature or angle at the needle shaft 120 deflects the needle tip 110 to the area of the mandibular foramen 14 where the anesthetic is deposited adjacent the inferior alveolar nerve 12 at the injection site 24. This step of the technique ultimately eliminates the concern of failing to contact bone due to ramus flare as depicted by the prior art needle tip 44 in prior art FIGS. 4B and 4C.

Figure 9A:
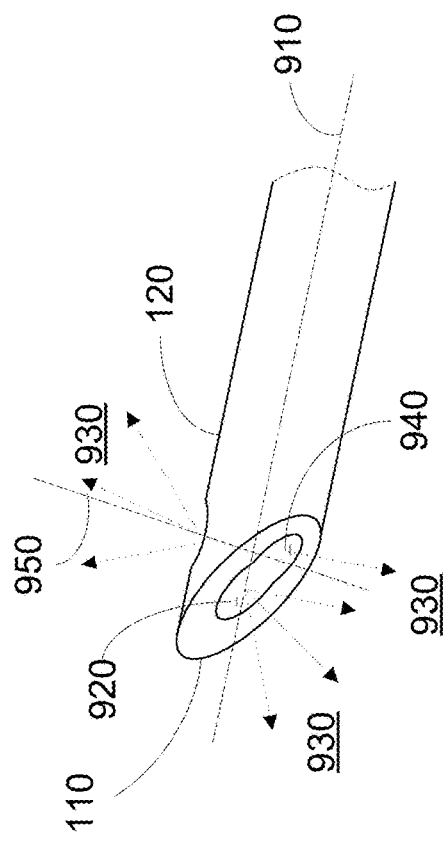
FIG. 9A is a side perspective view of a prior art needle tip.

The present invention provides improvements in the design of the tip 110 of the needle shaft 120. In the prior art needle as depicted in FIG. 9A, the tip 110 is formed by a ground surface angled with respect to the centerline 910 of the needle shaft 120 to form a sharp point. The anesthetic or other pharmaceutical compound used in the procedure passes thru the needle bore 920 running the length of the needle shaft 120 at the central axis 910 of the shaft 120. The pharmaceutical compound passing thru the needle assembly is depicted as arrows 930 leaving the needle bore 920.

Figure 9B:
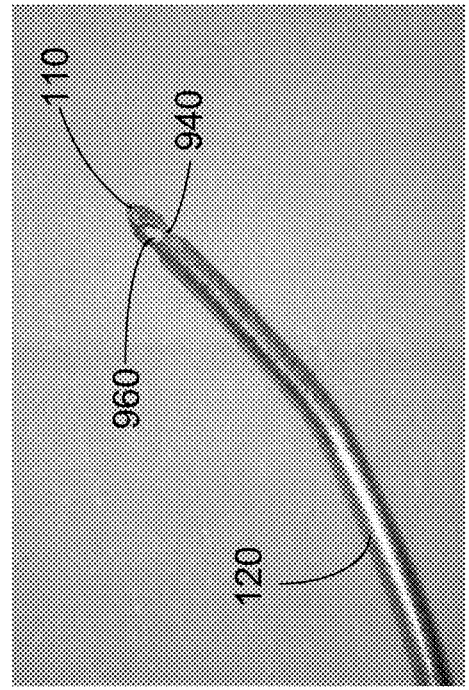
FIGS. 9B, 9C, and 9D are side perspective views of embodiments of the needle tip of the present invention.

In an embodiment of the present invention depicted in FIG. 9B, a hole or port 940 is formed proximate to the tip 120 and passing thru both the angled surface of the tip 120 and the central bore 920 along an axis depicted as 950. The axis 950 of the hole 940 may substantially bisect the angle between the ground surface of the angled tip 110 and the central axis 910 and passes thru both side walls of the needle shaft 120 and is in fluid connection with the needle bore 920. At least one additional port is formed as the hole 940 passes thru the sidewall of the needle shaft 120. As depicted in FIG. 9B in another alternative embodiment, a second port is partially formed as the hole 940 intersects the angled face of the needle tip 110 effectively increasing the cross sectional area of the central bore 920 proximate to the hole. The ports or holes 940 are in fluid interconnection with the central bore 920 and anesthetic or other pharmaceutical compound used in the procedure passes thru the needle bore 920 and leaves the needle out both the central bore 920 and the ports 940 and is depicted as arrows 930. In other alternative embodiments, the hole or bore 940 may be offset from the needle tip 110 and not intersect the angled face of the tip 110.

Figure 9C:
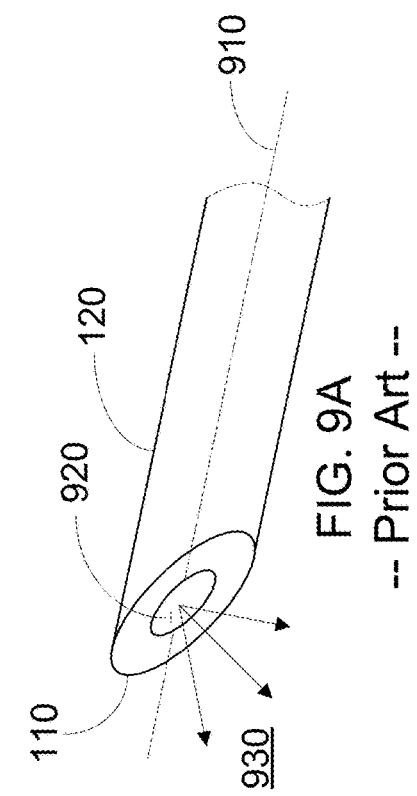

In another alternative embodiment depicted in FIG. 9C, a hole or port 960 is formed proximate to the tip 120 and passing thru the central bore 920 along the axis depicted as 970. The axis 970 of the hole 960 is perpendicular to the axis 910 of the central bore 920, and is parallel with the ground surface of the angled tip 110. The hole 960 intersects central bore 920 and passes thru both sidewalls of the needle shaft 120 to form two new holes or ports 960. The ports or holes 960 are in fluid interconnection with the central bore 920 and anesthetic or other pharmaceutical compound used in the procedure passes thru the needle bore 920 and leaves the needle out the central bore 920, the ports 940, and the ports 960 and is depicted as arrows 930. As depicted in FIG. 9C, this embodiment may incorporate the hole 940 of the embodiment of FIG. 9B. In an alternative embodiment, the hole 940 of the embodiment of FIG. 9B is not present.

Figure 9D:
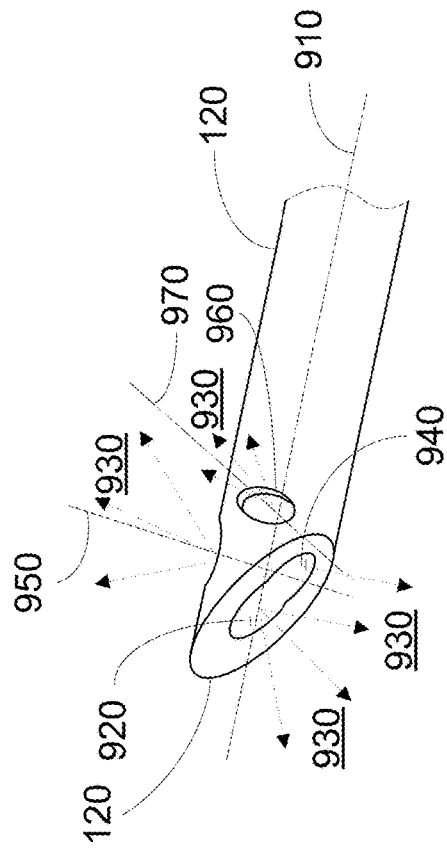

In yet another alternative embodiment depicted in FIG. 9D, the tip 110 of the needle shaft 120 is angled to a closed, but centered point. That tip 110 is preferably 3 mm in length. Where the tip ends and the shaft begins, a plurality of ports 940 and 960, or openings, for expulsion of anesthetic are formed into the tip 110 and shaft 120 junction. Each port is located at 90 degrees increments around the centerline of the needle. The tip 110 is continuous with the shaft 120 that extends to the hub 130. The central bore 920 of the shaft 120 and ports 940, 960 are in fluid interconnection and allow anesthetic to pass thru the shaft and out the ports at the injection site. As will be appreciated by those skilled in the art, the tip 110 may be between 1 mm and 5 mm in length. The tip may contain an additional axial opening for passing anesthetic thru the central bore 920 and out the tip 110 as in a conventional needle. The number of ports 940, 960 are preferably 4, but a single axial opening as in a conventional needle may be used, or a single or plurality of ports may be employed, or any combination thereof.

The design and location of the needle tip openings, or ports, of the embodiments of FIGS. 9B, 9C, and 9D allow for a "cloud" of anesthetic to be released radially from the axis of the needle tip at multiple locations in angles instead of a "stream" at a single angle primarily directed towards the intended anesthetic site. The anesthetic deposited in multiple radial directions provides a larger area for anesthetic deposition than a stream. The larger area of anesthetic deposition also compensates for anatomic variations between patients including the anterior/posterior location of the lingula as well as the lingula's inferior/superior location. The design also allows for a larger volume of anesthetic in the intended area of deposition as anesthetic is not deposited until after bone is contacted.

The curvature of the needle maximizes the effects of needle deflection to advantage to compensate for mandibular ramus flare and technique proficiency. Ultimately, the use of 3 landmarks, the curvature of the needle and the multiple ports at the needle tip work in tandem to dramatically reduce the learning curve and makes the inferior alveolar nerve block a predictable and reliable technique for mandibular anesthesia. The curved needle shaft 120 design of the present invention also improves the tactile feedback to the practitioner as the needle penetrates tissue and contacts bone.

While there has been shown a preferred embodiment of the present invention, it is to be understood that certain changes may be made in the forms and arrangement of the elements of the curved dental needle without departing from the underlying spirit, scope, and essential characteristics of the invention. The present embodiment is therefore, to be considered as merely illustrative and not restrictive, the scope of the invention being indicated by the claims rather than the foregoing description, and all changes which come within the meaning and range of equivalence of the claims are therefore intended to be embraced therein.

What is claimed is:

1. A needle assembly used in a dental procedure upon a patient, the dental procedure requiring injection of a pharmaceutical compound into an injection site at the posterior vertical wall of the patient mouth, the needle assembly being affixed to a syringe barrel for use, the syringe barrel housing a carpule containing a pharmaceutical compound, the needle assembly comprising:
   a needle shaft, the needle shaft comprising a central bore therein for passing pharmaceutical compounds there thru;
   a needle tip on one end of the needle shaft, the needle tip in fluid interconnection with the central bore;
   a hub and a syringe adaptor, adjacent the other end of the needle shaft opposing the needle tip, the needle shaft passing thru the hub and syringe adaptor, the syringe adaptor configured to engage the syringe barrel;
   the needle shaft extending beyond the syringe adaptor and configured to pierce the carpule upon engagement with the syringe barrel, the central bore of the needle shaft and the needle tip thereby in fluid interconnection with the pharmaceutical compound contained in the carpule;
   the needle shaft comprising a centerline axis and a curve therein such that the centerline axis of the needle shaft at the needle tip is at an angle when compared to the centerline axis of the needle shaft at the hub;
   wherein, as the needle tip is inserted into an injection site at the posterior vertical wall of the patient mouth and an axial force is applied to the syringe barrel, the centerline axis of the needle shaft at the needle tip deflects to a more perpendicular angle relative to the patient posterior vertical wall, for injection of the pharmaceutical compound proximate to the injection site.

2. The invention of claim 1, wherein the pharmaceutical compound is an anesthetic.

3. The invention of claim 1, wherein the dental procedure is an inferior alveolar nerve block.

4. The invention of claim 1, wherein the angled needle shaft centerline axis facilitates access to the injection site by avoiding physical obstacles presented by the patient anatomy to the needle assembly and syringe barrel.

5. The invention of claim 1, wherein the angle between the centerline axis of the needle shaft at the needle tip when compared to the centerline axis of the needle shaft at the hub is between 15 and 45 degrees.

6. The invention of claim 1, wherein the angle between the centerline axis of the needle shaft at the needle tip when compared to the centerline axis of the needle shaft at the hub is substantially 30 degrees.

7. The invention of claim 1, wherein the needle shaft has an internal gauge between 20 and 32.

8. The invention of claim 1, wherein the needle shaft has an internal gauge between 25 to 27.

9. The invention of claim 1, wherein the needle shaft has a length between 20 millimeters to 40 millimeters from the needle tip to the hub measured along the needle shaft centerline.

10. The invention of claim 1, wherein the needle tip further comprises a single axial hole and an angled tip.

11. The invention of claim 1, wherein the needle tip further comprises at least one port in fluid interconnection with the needle central bore for delivery of the pharmaceutical compound.

12. A needle assembly used in a dental procedure upon a patient, the dental procedure being injection of a pharmaceutical compound into an injection site at a posterior vertical wall of a patient mouth in an inferior alveolar nerve block procedure, the needle assembly being affixed to a syringe barrel for use, the syringe barrel housing a carpule containing a pharmaceutical compound, the needle assembly comprising:
   a needle shaft comprising a central bore between 25 and 27 gauge therein for passing pharmaceutical compounds there thru;
   a needle tip on one end of the needle shaft, the needle tip in fluid interconnection with the central bore;
   a hub and a syringe adaptor, adjacent the other end of the needle shaft opposing the needle tip, the needle shaft passing thru the hub and syringe adaptor, the syringe adaptor configured to engage the syringe barrel;
   the needle shaft extending beyond the syringe adaptor and configured to pierce the carpule upon engagement with the syringe barrel, the central bore of the needle shaft and the needle tip thereby in fluid interconnection with the pharmaceutical compound contained in the carpule;
   the needle shaft comprising a curve therein such that a centerline axis of the needle shaft at the needle tip is at a 30 degree angle when compared to the centerline axis of the needle shaft at the hub;
   wherein, as the needle tip is inserted into an injection site at the posterior vertical wall of the patient mouth and an axial force is applied to the syringe barrel, the centerline axis of the needle shaft at the needle tip deflects to a more perpendicular angle relative to the patient posterior vertical wall, for injection of the pharmaceutical compound proximate to the injection site.

* * * * *